(12) United States Patent
Park et al.

(10) Patent No.: US 11,439,982 B2
(45) Date of Patent: Sep. 13, 2022

(54) METHOD OF PRODUCING OLEFIN USING CIRCULATING FLUIDIZED BED PROCESS

(71) Applicants: SK GAS CO., LTD., Seongnam-si (KR); KOREA RESEARCH INSTITUTE OF CHEMICAL TECHNOLOGY, Daejeon (KR); KOREA NATIONAL UNIVERSITY OF TRANSPORTATION INDUSTRY-ACADEMIC COOPERATION FOUNDATION, Chungju-si (KR)

(72) Inventors: Yong Ki Park, Seoul (KR); Won Choon Choi, Daejeon (KR); Daesung Park, Daejeon (KR); Hawon Park, Daejeon (KR); Changyeol Song, Daejeon (KR); Deuk Soo Park, Yongin-si (KR); Ung Gi Hong, Seongnam-si (KR); Miyoung Lee, Seoul (KR); Sungwon Kim, Chungju-si (KR); Chaeeun Yeo, Chungju-si (KR)

(73) Assignees: SK GAS CO., LTD., Seongnam-si (KR); KOREA RESEARCH INSTITUTE OF CHEMICAL TECHNOLOGY, Daejeon (KR); KOREA NATIONAL UNIVERSITY OF TRANSPORTATION INDUSTRY-ACADEMIC COOPERATION FOUNDATION, Chungju-si (KR)

( * ) Notice: Subject to any disclaimer, the term of this patent is extended or adjusted under 35 U.S.C. 154(b) by 0 days.

(21) Appl. No.: 17/281,132

(22) PCT Filed: Dec. 4, 2019

(86) PCT No.: PCT/KR2019/016985
§ 371 (c)(1),
(2) Date: Mar. 29, 2021

(87) PCT Pub. No.: WO2020/138748
PCT Pub. Date: Jul. 2, 2020

(65) Prior Publication Data
US 2021/0354112 A1   Nov. 18, 2021

(30) Foreign Application Priority Data
Dec. 28, 2018 (KR) .................. 10-2018-0172303

(51) Int. Cl.
*B01J 21/06* (2006.01)
*B01J 8/38* (2006.01)
(Continued)

(52) U.S. Cl.
CPC ............. *B01J 21/066* (2013.01); *B01J 8/38* (2013.01); *B01J 21/04* (2013.01); *B01J 23/26* (2013.01);
(Continued)

(58) Field of Classification Search
CPC ... B01J 21/066; B01J 8/38; B01J 21/04; B01J 23/26; B01J 23/30; B01J 35/023;
(Continued)

(56) References Cited

U.S. PATENT DOCUMENTS

8,563,793 B2 * 10/2013 Zimmermann ........... C07C 5/05
585/654
2008/0194891 A1 * 8/2008 Pretz .................... C07C 5/3332
585/252
(Continued)

FOREIGN PATENT DOCUMENTS

KR        10-0651418 B1    11/2006
KR     10-2018-0133694 A   12/2018
(Continued)

OTHER PUBLICATIONS

International Search Report for PCT/KR2019/016985 dated Apr. 2, 2020 from Korean Intellectual Property Office.
(Continued)

Primary Examiner — Ali Z Fadhel
(74) Attorney, Agent, or Firm — Paratus Law Group, PLLC (57) ABSTRACT

Disclosed is a method of producing an olefin using a circulating fluidized bed process, including: (a) supplying a hydrocarbon mixture including propane and a dehydrogenation catalyst to a riser which is in a state of a fast fluidization regime, and thus inducing a dehydrogenation reaction; (b) separating an effluent from the dehydrogenation reaction into the catalyst and a propylene mixture; (c) stripping, in which a residual hydrocarbon compound is removed from the catalyst separated in step (b); (d) mixing the catalyst stripped in step (c) with a gas containing oxygen and thus continuously regenerating the catalyst; (e) circulating the catalyst regenerated in step (d) to step (a) and thus resupplying the catalyst to the riser; and (f) cooling, compressing, and separating the propylene mixture, which is a reaction product separated in step (b), and thus producing a propylene product.

26 Claims, 6 Drawing Sheets

(51) Int. Cl.
    | | |
    |---|---|
    | *B01J 21/04* | (2006.01) |
    | *B01J 23/26* | (2006.01) |
    | *B01J 23/30* | (2006.01) |
    | *B01J 35/02* | (2006.01) |
    | *B01J 35/10* | (2006.01) |
    | *B01J 37/08* | (2006.01) |
    | *C07C 5/333* | (2006.01) |

(52) U.S. Cl.
    CPC ............. *B01J 23/30* (2013.01); *B01J 35/023* (2013.01); *B01J 35/1014* (2013.01); *B01J 35/1019* (2013.01); *B01J 37/088* (2013.01); *C07C 5/3332* (2013.01); *C07C 2521/04* (2013.01); *C07C 2521/06* (2013.01); *C07C 2523/26* (2013.01); *C07C 2523/30* (2013.01)

(58) Field of Classification Search
CPC .. B01J 35/1014; B01J 35/1019; B01J 37/088; B01J 2208/00672; B01J 8/1809; B01J 8/1827; B01J 8/1863; B01J 8/388; B01J 2208/00017; B01J 2208/00557; B01J 2523/00; B01J 21/063; B01J 23/34; B01J 23/92; B01J 35/0006; B01J 38/02; B01J 38/12; B01J 37/0201; B01J 8/24; B01J 23/04; B01J 37/0234; B01J 37/0236; B01J 37/024; B01J 37/08; B01J 2208/00548; C07C 5/3332; C07C 2521/04; C07C 2521/06; C07C 2523/26; C07C 2523/30; C07C 5/48; C07C 7/11; C07C 9/08; C07C 11/06; Y02P 20/52; Y02P 20/584

See application file for complete search history.

(56) References Cited

U.S. PATENT DOCUMENTS

| | | | |
|---|---|---|---|
| 2009/0012339 A1* | 1/2009 | Choi | .................... C07C 7/04 |
| | | | 585/651 |
| 2018/0079700 A1* | 3/2018 | Pretz | .................... B01J 8/26 |

FOREIGN PATENT DOCUMENTS

| | | | | |
|---|---|---|---|---|
| KR | 10-2018-0133695 A | | 12/2018 | |
| WO | WO-2014081545 A1 * | | 5/2014 | ............. B01J 19/32 |

OTHER PUBLICATIONS

Sangseo Gu et al., "Effects of metal or metal oxide additives on oxidative coupling of methane using $Na_2WO_4/SiO_2$ catalysts: Reducibility of metal additives to manipulate the catalytic activity", Applied Catalysis A, General, May 25, 2018, pp. 114-119, vol. 562.

Jianqiang Zhu et al., "$Na_2WO_4/Mn/SiO_2$ catalyst for oxidative dehydrogenation of ethane using $CO_2$ as oxidant", Catalysis Today, Aug. 13, 2019, pp. 310-315, vol. 148, Nos. 3-4.

* cited by examiner

METHOD OF PRODUCING OLEFIN USING CIRCULATING FLUIDIZED BED PROCESS

CROSS-REFERENCE TO PRIOR APPLICATIONS

This application is a National Stage Patent Applications of PCT International Patent Application No. PCT/KR2019/016985 (filed on Dec. 4, 2019) under 35 U.S.C. § 371, which claims priority to Korean Patent Application No. 10-2018-0172303 (filed on Dec. 28, 2018), which are all hereby incorporated by reference in their entirety.

BACKGROUND

The present invention relates to a method of producing an olefin using a circulating fluidized bed process.

Olefins, such as ethylene and propylene, are widely used in the petrochemical industry. In general, these olefins are obtained in a naphtha thermal cracking process. However, as the competitiveness of processes using lower hydrocarbons as raw materials has increased due to the shale gas revolution and the like, an on-purpose olefin producing process based on a catalytic dehydrogenation process is required.

Catalytic dehydrogenation processes for olefin production use various lower hydrocarbon compounds as raw materials, and produce olefins in high yields. However, commercial fixed-bed dehydrogenation processes have problems in that although olefin yield is high at the initial stage of a reaction in which a hydrocarbon comes into contact with a catalyst, a hydrocarbon conversion and olefin yield generally decrease over time due to the deactivation of the catalyst and the generation of an excessive amount of coke, and a lot of energy is consumed in a regeneration process. To solve these problems, circulating fluidized bed processes in which the contact time between a hydrocarbon and a catalyst is limited to a short time have been proposed.

However, even in the processes in which the contact time between a hydrocarbon and a catalyst is limited, by-products besides an olefin are generated through a reaction between the hydrocarbon and the catalyst at the initial stage of a reaction, so the conversion of a reaction raw material is high, but there is also the disadvantage of very low selectivity.

In a process of producing an olefin from a mixture of hydrocarbon raw materials through a circulating fluidized bed process, in order to enhance conversion and selectively produce an olefin such as ethylene or propylene with high selectivity, the setting of operating conditions of a riser where a dehydrogenation reaction is mainly performed may be considered an important factor. In particular, the flow and reaction phenomena occurring in a riser tube can be more easily understood through the following theoretical considerations and will be described in more detail below.

Figure 1:
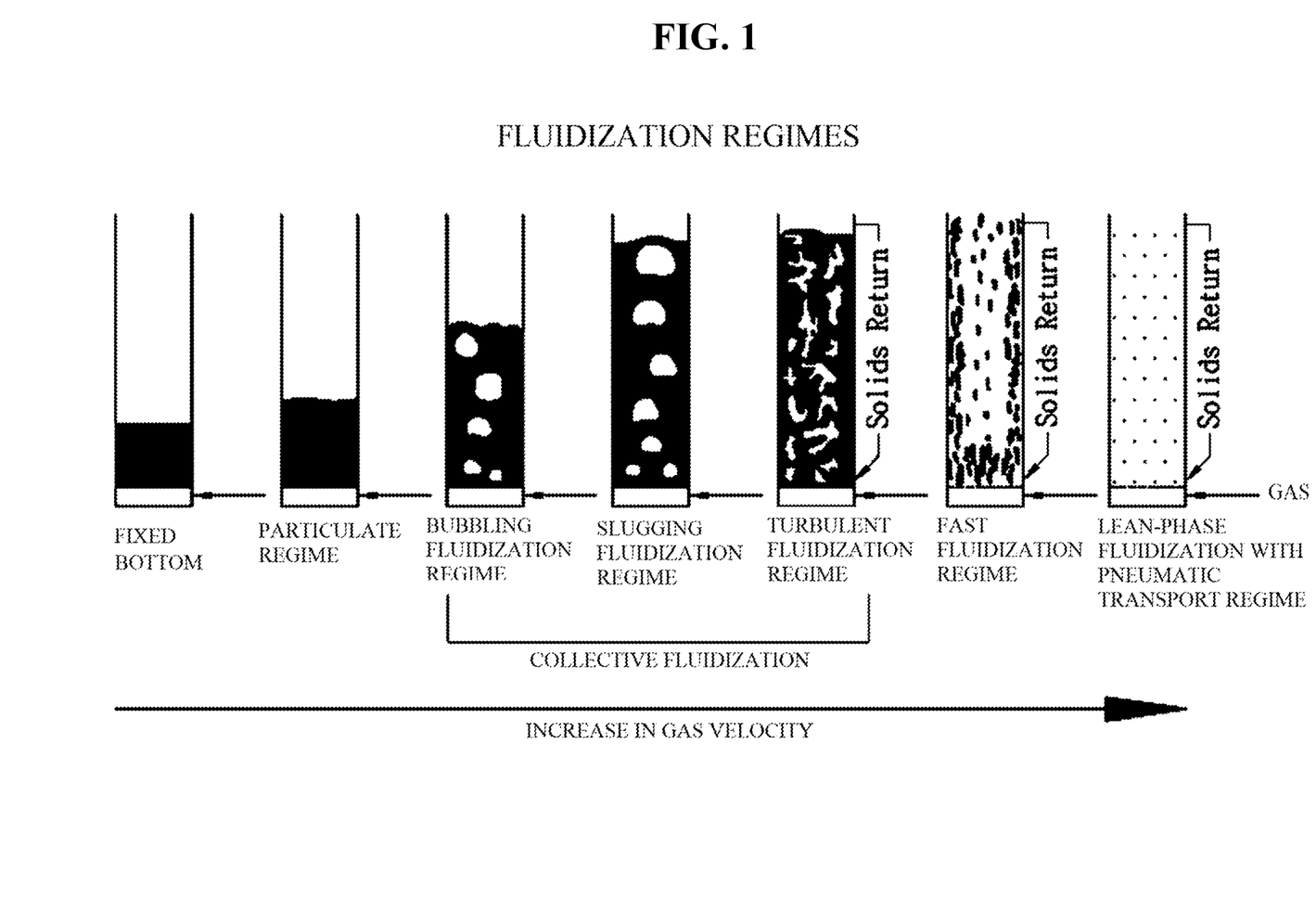
FIG. 1 is an image for illustrating a typical change in internal fluidized bed characteristics with respect to a flow regime as a gas velocity changes.

When gas is introduced into a container filled with a solid catalyst through the bottom of the container as shown in FIG. 1, particles are fluidized, and when a minimum fluidization velocity is exceeded, flow regimes are exhibited, which are typically divided into five regimes.

Specifically, the five regimes are respectively referred to as a minimum fluidization regime, a bubbling fluidization regime, a slugging fluidization regime, a turbulent fluidization regime, and a lean-phase fluidization with pneumatic transport regime, and these regimes differ in the way the particles move.

Therefore, in the case of processes carried out using a fluidized bed reactor, flow regimes suitable for characteristics of each process are created to carry out the process.

Figure 2:
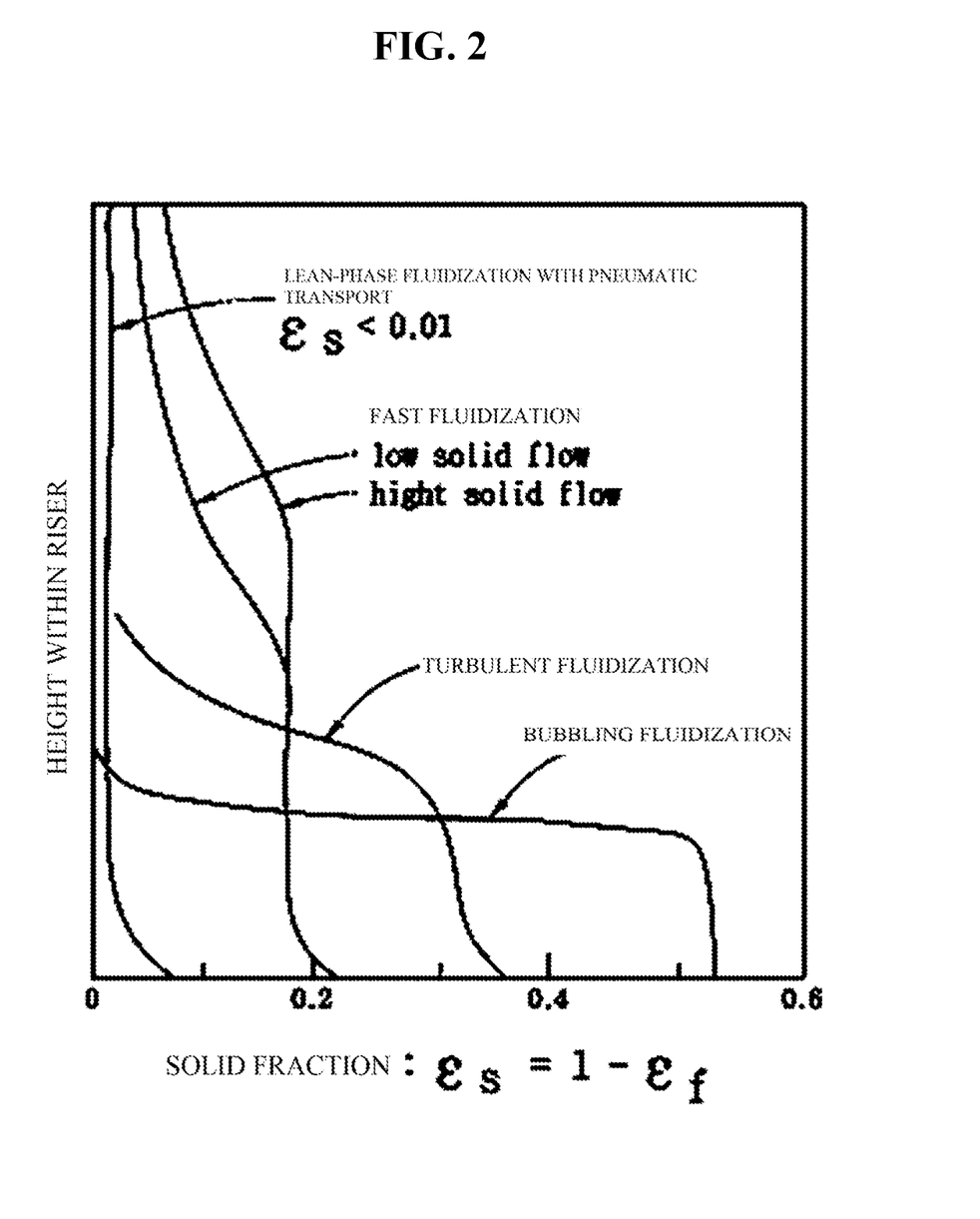
FIG. 2 is an image for illustrating a catalyst volume fraction inside a fluidized bed according to the height within a riser.

FIG. 2 shows a change in catalyst volume fraction in a reactor according to a change in height within a riser, that is, a change in flow regime, and it can be seen that the catalyst volume fraction in the reactor changes as the flow regime changes. However, in a catalytic reaction such as a fluidized-bed catalytic dehydrogenation reaction process, since the catalyst volume fraction has a significant impact on process performance, the process operating conditions, which determine the flow regime by controlling the catalyst volume fraction in the reactor, have a very significant impact on the outcome of the reaction.

The following factors should be taken into account when determining the flow regime of a riser used in the circulating fluidized bed process: a catalyst size, a catalyst circulation rate, a catalyst-to-feedstock ratio, and catalyst strength.

In addition, the following factors that directly affect the dehydrogenation reaction should be taken into account: a reaction temperature, an amount of heat absorbed in the reaction, a reaction time, and catalyst deactivation due to coke formation.

The existing FPDH (Fluidized Propane DeHydrogenation) process being developed aims to limit the catalyst residence time to 10 seconds or less. When the catalyst residence time is short, not only is a feed rate of propane feedstock high, but also the catalyst is immediately regenerated and again allowed to participate in a reaction, so when such a process is developed for commercial use, propylene production can be greatly increased compared to in a fixed bed process.

However, in this case, since a contact time between the catalyst and propane is short, catalyst efficiency becomes very important. That is, it is important to maximize both selectivity and a conversion rate, which are two measures of catalyst efficiency.

Furthermore, the currently used propane dehydrogenation techniques are configured based on a precious metal catalyst or an intermittent process, and even techniques based on a continuous process have problems with the operation of a catalyst bed and thus are known to be unsuitable for the mass production of propylene on the scale of millions of tons. In addition, a propane dehydrogenation reaction has a thermodynamic limit of propane conversion due to a reverse reaction of the produced propylene and hydrogen. Therefore, in order to effectively mass-produce propylene, it is required to develop a new propane dehydrogenation process in which the above-described problem of a continuous process is solved, an inexpensive non-precious metal catalyst with maximized selectivity and conversion is used, and thus production costs are reduced.

Among the catalysts used for propane dehydrogenation, in the case of a precious metal catalyst, a reaction proceeds through a direct dehydrogenation mechanism in which hydrogen is adsorbed onto an active site, but in the case of a transition metal, since an active site is imperfect due to the mobility of electrons, a reaction mechanism has not been clearly identified.

Under these circumstances, the most commonly used catalysts as PDH catalysts are Pt, Pt—Sn, VOx, and CrOx catalysts, and the CrOx catalysts are very excellent in terms of a propane conversion and selectivity. On the other hand, the Pt catalysts have excellent selectivity but are expensive and have very low conversion.

The CrOx catalysts, which are representative oxide catalysts, have forms in which $Cr^{6+}$ and $Cr^{3+}$ are stable, and the catalysts produced by calcining at high temperature are mostly $Cr_2O_3$, that is, $Cr^{3+}$, but some $Cr^{6+}$ is present. In the prepared catalyst (new catalyst), the oxygen generated by the reduction of $Cr^{6+}$ to $Cr^{3+}$ at the beginning of a reaction (i.e., generated from a lattice oxygen of an oxidation catalyst) participates in a propane dehydrogenation reaction and thus contributes to the production of $CO_2$ rather than propylene.

However, in a fluidized bed reactor, since a catalyst residence time is 10 seconds or less, the generation of $CO_2$ due to the complete oxidation of propane over a transition metal oxide catalyst at the beginning of a reaction becomes a major problem, so in order to secure selectivity for propylene, it is essential to control the oxidation level of the transition metal. After all, in the case of an FPDH process using a fluidized bed reactor, the selectivity issue is very important because of the short reaction time.

Hence, the inventors of the present invention have studied a method of producing an olefin using a circulating fluidized bed process having higher economic efficiency and higher productivity than the conventional producing process and a catalyst used therefor, and have found that the problems of the conventional technique can be solved by introducing a promoter. Therefore, the inventors have developed a more efficient olefin producing method by applying a catalyst for olefin production having both an excellent conversion and excellent selectivity to a circulating fluidized bed process, and thus completed the present invention.

SUMMARY

The present invention is directed to providing an olefin production process using a fluidized bed, which has higher economic efficiency and higher productivity than the conventional process.

A method of producing an olefin using a circulating fluidized bed process according to the present invention includes:

(a) supplying a hydrocarbon mixture including propane and a dehydrogenation catalyst to a riser which is in a state of a fast fluidization regime, and thus inducing a dehydrogenation reaction;

(b) separating an effluent from the dehydrogenation reaction into the catalyst and a propylene mixture;

(c) stripping, in which a residual hydrocarbon compound is removed from the catalyst separated in step (b);

(d) mixing the catalyst stripped in step (c) with a gas containing oxygen and thus continuously regenerating the catalyst;

(e) circulating the catalyst regenerated in step (d) to step (a) and thus resupplying the catalyst to the riser; and (f) cooling, compressing, and separating the propylene mixture, which is a reaction product separated in step (b), and thus producing a propylene product, wherein the dehydrogenation catalyst preferably includes: a support including alumina and an auxiliary support component; and a main catalyst including an active metal supported on the support, and includes or does not include a promoter including an alkali metal and a Group 6B transition metal.

Preferably, the fast fluidization regime is a fluidization regime in which a dense region is present at a lower portion of the riser and a dilute region is present at an upper portion of the riser, and is a steady state in which a fixed amount of catalyst is continuously introduced into the riser while a gas flow rate in the riser is maintained to be higher than in a turbulent fluidization regime and lower than in a lean-phase fluidization with pneumatic transport regime.

Preferably, in the fast fluidization regime, a) a gas velocity that is no less than a gas flow rate required for the catalyst continuously introduced through the lower portion of the riser to be entrained and smoothly discharged through the upper portion of the riser is maintained, and b) the gas velocity and a catalyst injection rate are adjusted so that the catalyst volume fraction difference between two points is maintained within the range of 0.02 to 0.04.

Also, the catalyst volume fraction difference between a ¼ point and a ¾ point from the bottom of the riser is preferably maintained within the range of 0.02 to 0.04.

The hydrocarbon mixture preferably includes propane in an amount of 90% by weight or more and more preferably includes propane in an amount of 95% by weight or more.

An average size of the catalyst is preferably in the range of 20 to 200 microns and more preferably in the range of 60 to 120 microns.

Preferably, the temperature of the lower portion of the riser is in the range of 500 to 650° C., the temperature of the upper portion of the riser is in the range of 450 to 600° C., and the temperature of the lower portion of the riser is maintained to be higher than the temperature of the upper portion of the riser.

The pressure in the riser is preferably maintained within the range of −1 to 5 $kg/cm^2 \cdot g$.

For the dehydrogenation reaction to occur in the riser, the residence time of the hydrocarbon mixture in the riser is maintained within the range of 0.1 to 500 seconds, preferably 0.1 to 50 seconds, and more preferably 0.5 to 5 seconds.

In the method of producing an olefin according to the present invention, the weight ratio obtained by dividing the weight of the catalyst resupplied to the lower portion of the riser in step (e) by the weight of the hydrocarbon mixture is in the range of 10 to 100 and preferably 20 to 60.

In the dehydrogenation catalyst according to the present invention, the auxiliary support component preferably includes one or more selected from among zirconium and phosphorus (P).

Zirconium is particularly preferable as the auxiliary support component, and preferably, the molar ratio of the zirconium to aluminum (i.e., Zr:Al) in the alumina is in the range of 0.01 to 0.1.

The active metal component preferably includes one or more selected from chromium, vanadium, manganese, iron, cobalt, molybdenum, copper, zinc, cerium, and nickel.

Chromium is particularly preferable as the active metal component, and preferably, chromium accounts for 1 to 20% of the weight of the catalyst.

The alkali metal is preferably sodium.

The Group 6B transition metal is preferably tungsten.

The promoter is preferably included in an amount of 0.01% by weight or more and less than 1% by weight.

Preferably, the alumina support has a γ or θ phase and a surface area of 80 to 300 $m^2/g$ in a producing temperature range of 550 to 850° C., which is greater than or equal to the dehydrogenation reaction temperature.

A dehydrogenation catalyst used in the method of producing an olefin according to the present invention includes:

providing a support including an auxiliary support component and alumina;

allowing a main catalyst including an active metal to be supported; and drying and calcining the support on which the main catalyst is supported, wherein, when a promoter is to be additionally supported, the dehydrogenation catalyst is preferably prepared by mixing the promoter including an alkali metal and a Group 6B transition metal with the support at the same time as the main catalyst, or by impregnating the promoter into the support immediately after the drying and then performing drying and calcining, or by impregnating the promoter into the support immediately after the calcining and then performing drying and calcining.

The drying is preferably performed at a temperature of 100 to 150° C.

The calcining is preferably performed at a temperature of 700 to 850° C.

The present invention relates to a circulating fluidized bed process in which an olefin is produced from a hydrocarbon raw material by using a catalyst for producing an olefin according to the present invention in a fast fluidized bed, and since the raw material comes into effective contact with the catalyst in the fast regime, a conversion is increased and yield is increased, and therefore, the production of an olefin can be more efficiently increased.

That is, in the circulating fluidized bed process of the present invention, since yield is improved compared to in conventional commercial processes, incremental profits from raw materials increase, and since a continuous reaction-regeneration fluidized bed reactor is used and thus a direct heat supply method is used in the regeneration process, a small amount of air flow and a small air compressor are required, so fuel consumption is reduced by 10 to 15% and compressor energy essential for product separation and catalyst regeneration is reduced by 15 to 20% compared to in the commercial processes, and thus overall production costs are reduced.

DETAILED DESCRIPTION

A method of producing an olefin using a circulating fluidized bed process according to the present invention includes:

(a) supplying a hydrocarbon mixture including propane and a dehydrogenation catalyst to a riser which is a fast fluidization regime, and thus inducing a dehydrogenation reaction;

(b) separating an effluent from the dehydrogenation reaction into the catalyst and a propylene mixture;

(c) stripping, in which a residual hydrocarbon compound is removed from the catalyst separated in step (b);

(d) mixing the catalyst stripped in step (c) with a gas containing oxygen and thus continuously regenerating the catalyst;

(e) circulating the catalyst regenerated in step (d) to step (a) and thus resupplying the catalyst to the riser; and (f) cooling, compressing, and separating the propylene mixture, which is a reaction product separated in step (b), and thus producing a propylene product, wherein the dehydrogenation catalyst preferably includes: a support including alumina and an auxiliary support component; and a main catalyst including an active metal supported on the support, and includes or does not include a promoter including an alkali metal and a Group 6B transition metal.

A dehydrogenation catalyst used in the method of producing an olefin according to the present invention is produced by a method including:

providing a support including an auxiliary support component and alumina;

allowing a main catalyst including an active metal to be supported; and drying and calcining the support on which the main catalyst is supported, wherein, when a promoter is to be additionally supported, the dehydrogenation catalyst is preferably prepared by mixing the promoter including an alkali metal and a Group 6B transition metal with the support at the same time as the main catalyst, or by impregnating the promoter into the support immediately after the drying and then performing drying and calcining, or by impregnating the promoter into the support immediately after the calcining and then performing drying and calcining.

Hereinafter, exemplary embodiments of the present invention will be described with reference to the accompanying drawings. However, the embodiments of the present invention can be variously modified, and the scope of the present invention is not limited to the embodiments described below.

In describing the embodiments of the present invention, the same names and reference numerals are used for the same configurations, and any overlapping descriptions will be omitted. The drawings referenced below are not to scale.

A method of producing an olefin using a circulating fluidized bed process according to the present invention includes:

(a) supplying a hydrocarbon mixture including propane and a dehydrogenation catalyst to a riser which is a fast fluidization regime, and thus inducing a dehydrogenation reaction;

(b) separating an effluent from the dehydrogenation reaction into the catalyst and a propylene mixture;

(c) stripping, in which a hydrocarbon compound is removed from the catalyst separated in step (b);

(d) mixing the catalyst stripped in step (c) with a gas containing oxygen and thus continuously regenerating the catalyst;

(e) circulating the catalyst regenerated in step (d) to step (a) and thus resupplying the catalyst to the riser; and (f) cooling, compressing, and separating the propylene mixture, which is a reaction product separated in step (b), and thus producing a propylene product, wherein the dehydrogenation catalyst preferably includes: a support including alumina and an auxiliary support component; and a main catalyst including an active metal supported on the support, and includes or does not include a promoter including an alkali metal and a Group 6B transition metal.

Hereinafter, one embodiment of a catalytic cracking process will be described in more detail with reference to the accompanying FIG. 3, but the scope of the present invention is not limited thereto.

Figure 3:
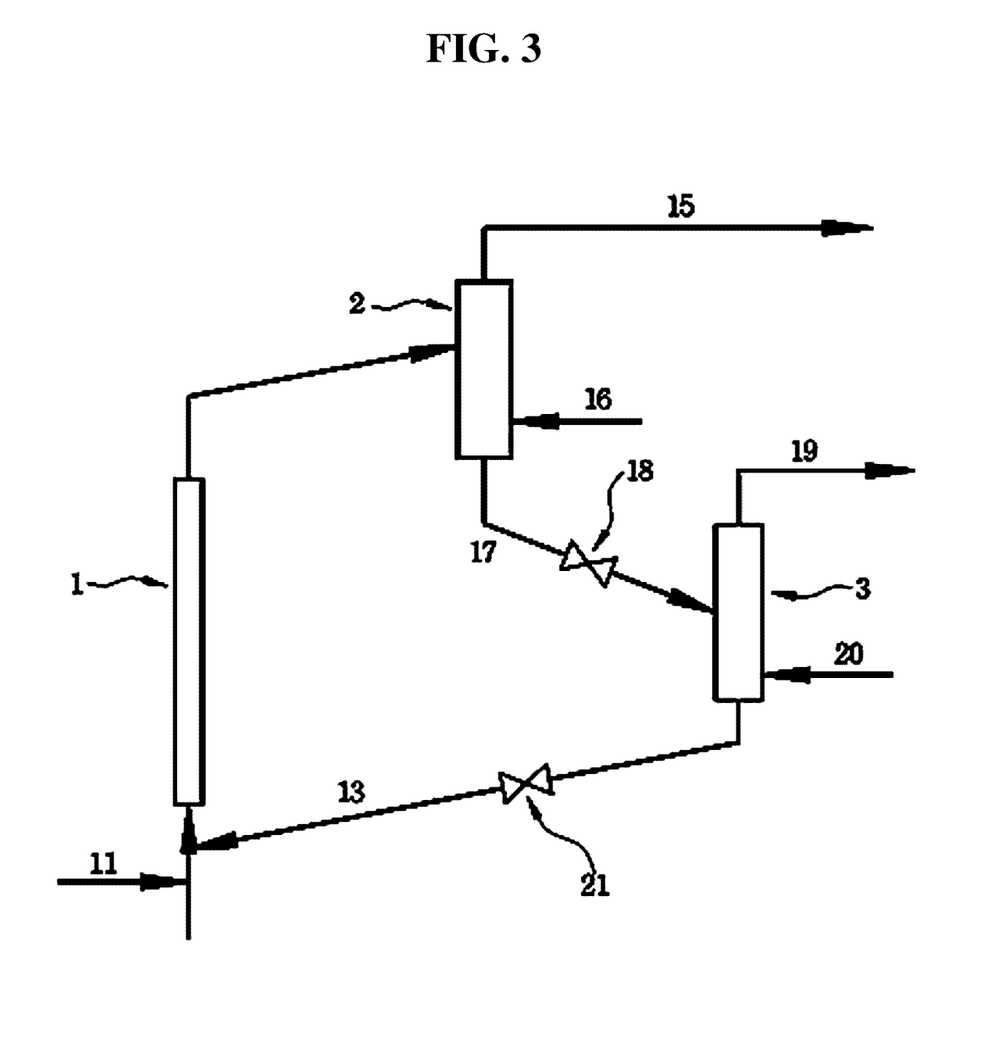
FIG. 3 is an image for schematically illustrating a circulating fluidized bed process used in the present invention.

The above-described hydrocarbon mixture feedstock is supplied through a line 11 of FIG. 3, and in this case, the feedstock may be heated to a temperature of 30 to 600° C. for a smoother reaction and supplied. In addition, depending components thereof, the feedstock may be supplied as a gas or in a liquid dispersion form, but the present invention is not particularly limited thereto.

The feedstock of the line 11 is introduced into a riser 1 which is a reaction zone, and is mixed with a regenerated catalyst supplied through a regenerator stand pipe (line 13) at a lower portion of the riser 1. In addition, a process of mixing the feedstock and the regenerated catalyst can be variously configured by methods known in the art, and all of these configurations are included in the scope of the present invention.

Meanwhile, a catalyst used in the process is regenerated in a regenerator 3, and the regenerated catalyst is supplied to the riser 1 through the line 13, and at this time, the temperature of the lower portion of the riser is preferably maintained within the range of 500 to 650° C. That is, by the amount of heat supplied by the regenerated catalyst 13, the temperature of the feedstock 11 is raised to a temperature required for a dehydrogenation reaction. When the temperature of the lower portion of the riser is less than 500° C., a conversion of the catalyst is reduced, and when the temperature is more than 650° C., since more by-products are produced due to the pyrolysis of a hydrocarbon mixture which is a raw material, the selectivity of the catalyst is reduced.

Subsequently, the feedstock and the dehydrogenation catalyst mixed in the lower portion of the riser 1 are fluidized and flow upward as a dehydrogenation reaction occurs in the riser 1. In this case, as the endothermic dehydrogenation reaction proceeds, the temperature of the mixture is lowered, causing the temperature of an upper portion of the riser 1 to be relatively decreased.

The reaction product and the catalyst that have reached the upper portion of the riser 1 are introduced into a stripper 2 and thus are separated from each other within a short time. In order to increase the efficiency of this separation process, a cyclone may optionally be used.

The separated reaction product which is in a gaseous state is discharged through a line 15, and the separated catalyst accumulates in the stripper 2 and is moved downward. In this case, stripping steam is supplied to a lower portion of the stripper 2 through a line 16, and as the stripping steam 16 moves upward along the stripper 2, the unseparated hydrocarbon reaction product contained in the catalyst is removed and discharged through the line 15 configured for a gaseous reaction product.

The catalyst that has reached the lower portion of the stripper 2 is moved to the regenerator 3 through a stripper stand pipe (line 17) by the regulation of a slide valve 18. At this time, the catalyst may contain coke generated during the reaction. A gas, such as air containing oxygen, is introduced into the regenerator 3 through a line 20, and the coke contained in the catalyst is reacted with the oxygen at a high temperature of 500° C. or more and thus converted to carbon monoxide or carbon dioxide and then discharged as a flue gas through a line 19. As a result, the amount of coke contained in the catalyst may be significantly lowered.

Meanwhile, the regenerated catalyst present in a lower portion of the regenerator 3 is reintroduced into the riser through the regenerator stand pipe (line 13) by the regulation of a slide valve 21 so that the regenerated catalyst can be recirculated in the process.

In the process of the present invention, a hydrocarbon mixture and specifically a hydrocarbon mixture including propane in an amount of 90% by weight or more may be used as the feedstock. More preferably, a hydrocarbon mixture including propane in an amount of 95% by weight is used as the feedstock. When the concentration of the propane is low, catalyst selectivity is lowered due to side reactions of other impurities, and thus productivity is reduced.

The dehydrogenation catalyst that can be used to dehydrogenate the feedstock in the present invention is not particularly limited as long as it is a catalyst generally known in the art as being capable of converting a hydrocarbon compound to an olefin by a dehydrogenation reaction, but a catalyst which includes a support including alumina and an auxiliary support component and a main catalyst including an active metal supported on the support and includes or does not include a promoter including an alkali metal and a Group 6B transition metal is preferable.

Preferably, the auxiliary support component includes one or more selected from among zirconium and phosphorus (P).

Zirconium is particularly preferable as the auxiliary support component, and preferably, the molar ratio of the zirconium to aluminum (i.e., Zr:Al) in the alumina is in the range of 0.01 to 0.1.

The catalyst of the present invention has improved durability due to the auxiliary support component, and has an excellent function of exciting C—H bonds of a paraffin raw material as compared to a case using only alumina as a support. The catalyst provides an excellent hydrocarbon conversion and an excellent olefin yield and improves the selectivity for an olefin. In particular, zirconium serves to improve the durability of the alumina support.

When the molar ratio of the auxiliary support component, particularly zirconium, to aluminum is less than 0.01, the effect of improving durability is not exhibited, and when the molar ratio exceeds 0.1, since the surface area of the alumina support is significantly reduced, the supported active metal component cannot be polydispersed.

The active metal component preferably includes one or more selected from chromium, vanadium, manganese, iron, cobalt, molybdenum, copper, zinc, cerium, and nickel.

Chromium is particularly preferable as the active metal component, and preferably, chromium accounts for 1 to 20% of the weight of the catalyst.

When the active metal component is less than 1% by weight, the desired activity cannot be attained, and when the active metal component exceeds 20% by weight, a main active phase among chromium may decrease due to metal-support interactions and excessive metal binding ability, which is not desirable.

Preferably, the alumina support has a γ or θ phase and a surface area of 80 to 300 m$^2$/g in a producing temperature range of 550 to 850° C., which is greater than or equal to the dehydrogenation reaction temperature.

When the support is produced at a temperature lower than a dehydrogenation reaction temperature, the catalyst may be thermally transformed during a dehydrogenation reaction, and when the support is produced at a temperature above 850° C., the support may become crystallized, causing the surface area of the catalyst to be reduced, and thus when the catalyst comes into contact with a reactant, the transfer of catalytically active materials may be inhibited.

The alkali metal is preferably sodium.

The Group 6B transition metal is preferably tungsten.

The promoter is preferably included in an amount of 0.01% by weight or more and less than 1% by weight. When the amount of promoter is less than 0.01% by weight, the effect of increasing the selectivity of the active metal catalyst for propylene is insignificant, and when the amount of promoter is more than 1% by weight, a propane conversion is significantly decreased.

A method of producing a catalyst for olefin production according to the present invention includes:

providing a support including an auxiliary support component and alumina;

allowing a main catalyst including an active metal and an auxiliary active metal to be supported; and drying and calcining the support on which the main catalyst is supported, wherein, when a promoter is to be additionally impregnated, the dehydrogenation catalyst is preferably prepared by mixing the promoter including an alkali metal and a Group 6B transition metal with the support at the same time as the main catalyst, or by impregnating the promoter into the support immediately after the drying and then performing drying and calcining, or by impregnating the promoter into the support immediately after the calcining and then performing drying and calcining.

The drying is preferably performed at a temperature of 100 to 150° C. When the drying is performed at a temperature of less than 100° C., the solvent is not sufficiently dried, and when the drying is performed at a temperature of more than 150° C., the catalyst may be sintered with the support, which is undesirable.

The calcination is preferably performed at a temperature of 700 to 850° C. When the calcination is carried out at a calcining temperature of less than 700° C., the catalyst may have low thermal stability within a fluidized bed regeneration process temperature range of 600 to 700° C., and when the calcination is carried out at a calcining temperature of more than 850° C., the alumina oxide support of the catalyst may be phase-shifted, and thus the function of the support may be degraded.

Furthermore, the average size of the catalyst is preferably in the range of 20 to 200 microns and more preferably in the range of 60 to 120 microns. For the high-efficiency catalytic reaction, an appropriate fast fluidization regime which is intermediate between a turbulent fluidization regime and a lean-phase fluidization with pneumatic transport regime is required, but in a regime where the size of the catalyst is less than 20 microns, lean-phase fluidization predominates, and thus yield may be reduced due to a high space velocity. On the other hand, in a regime where the size of the catalyst is more than 200 microns, since the rate of product production is lowered due to excessively slow circulating fluidization, a very large catalytic reaction facility is needed to maintain the same productivity, and in this case, an economic rate of return is reduced.

As described above, a dehydrogenation reaction for converting a hydrocarbon compound raw material to an olefin takes place in the riser 1, and accordingly, the olefin yield is significantly affected by reaction conditions such as a riser temperature, a reactant residence time in the riser, and a catalyst volume fraction and distribution in the riser, which will be described in more detail below.

First, the riser temperature is highest at the bottom and decreases toward the top. In addition, in a circulating fluidized bed for implementing a continuous reaction-regeneration process, an upper portion temperature of the riser determines a regeneration temperature. Therefore, in the present invention, it is effective to maintain a lower portion temperature of the riser within the range of 500 to 650° C. and more preferably 550 to 630° C. When the temperature is 500° C. or less, initial catalyst activity may be lowered, and when the temperature is 650° C. or more, the pyrolysis of a raw material may occur in the riser, resulting in raw material loss. In addition, it is effective to maintain the upper portion temperature of the riser within the range of 450 to 600° C. and more preferably 520 to 580° C. When the upper portion temperature is 450° C. or less, temperature recovery may be inhibited in a process carried out in a regeneration unit of the circulating fluidized bed reactor, and when the upper portion temperature is 600° C. or more, overheating may occur while removing catalytic coke in the regeneration unit, making it impossible to control the lower portion temperature of the riser. However, for smooth flow, the lower portion temperature of the riser should be maintained to be higher than the upper portion temperature of the riser.

Meanwhile, the pressure in the riser is maintained within the range of −1 to 5 kg/cm²·g. The pressure in the riser refers to a reaction pressure, and when the pressure is lower than −1 kg/cm²·g, the compression energy for separating a product from the reaction products increases, and since the cost of investing in compression equipment also increases, overall economic efficiency is lowered. On the other hand, when the pressure in the riser is greater than 5 kg/cm²·g, the cost of investing in compression equipment provided at a rear end of the reactor and compression energy are reduced, but product yield is lowered because a high-pressure reaction takes place in the riser. Therefore, an appropriate pressure in the riser that falls within the above-described range is required.

In addition, in the case of a dehydrogenation process in which an olefin is produced using the catalyst, a reactant residence time in the riser may also be an important reaction condition that determines olefin yield and composition. Since the dehydrogenation reaction takes place in the riser, a reactant residence time in the riser determines the number of gas molecules and a flow rate, so it is necessary to establish a standard for determining the residence time. Therefore, in the present invention, a numerical value obtained by dividing riser volume by the volume velocity of gas discharged from the upper portion of the riser is used as the standard for determining the residence time in the riser.

In the present invention, a hydrocarbon compound raw material residence time in the riser that is effective for a dehydrogenation reaction is in the range of 0.1 to 500 seconds, preferably 0.1 to 50 seconds, and more preferably 0.5 to 5 seconds. When the residence time is less than 0.1 seconds, since it is impossible to secure sufficient contact time between the catalyst and a hydrocarbon raw material, product yield is lowered, and when the residence time is more than 500 seconds, the cost of investing in a reactor for implementing the fast fluidization regime required by the present invention becomes excessively high.

The fluidized bed dehydrogenation reaction of the present invention is an endothermic reaction, and the amount of heat required for the reaction is supplied by recirculating a hot catalyst. Therefore, in the present invention, as for the amount of catalyst recirculation that is more suitable for this purpose, it is effective when a weight ratio obtained by dividing the weight of recirculated catalyst by the weight of the feedstock (hydrocarbon mixture including liquefied petroleum gas (LPG)) is in the range of 10 to 100 and preferably 20 to 60.

When the weight ratio is less than 10, since a hydrocarbon raw material is fed with an excessively high space velocity, sufficient contact time cannot be secured, and when the weight ratio is greater than 100, the cost of investing in a reactor for implementing the fast fluidization regime required by the present invention is excessively high. In addition, since excessive flow is caused in the catalyst regeneration unit and thus sufficient regeneration time cannot be secured, it is required that the catalyst weight divided by the weight of the hydrocarbon mixture satisfies the above-described appropriate weight ratio range.

Meanwhile, as described above, a catalyst volume fraction and distribution in the riser are greatly affected by the flow regime, and here, the flow regime is affected by the gas velocity in the riser and the rate of catalyst injection into the riser.

According to a circulating fluidized bed process of the present invention, in order to effectively produce an olefin-based hydrocarbon compound from a hydrocarbon raw material mixture, it is important to provide a sufficient catalyst volume fraction and distribution for the dehydrogenation reaction to occur by maintaining a fast fluidization regime as the fluidization regime of the riser.

Therefore, there is a need to more clearly define the range of the fast fluidization regime, and for this, the fast fluidization regime will be described by way of comparing two adjacent fluidization regimes, that is, a turbulent fluidization regime and a lean-phase fluidization with pneumatic transport regime. First, as a gas flow rate increases in the turbulent fluidization regime, solid particles become markedly entrained and are discharged from the riser, and thus a transition to the fast fluidization regime occurs. Therefore, in order to maintain a specific amount of catalyst in the riser at the gas velocity of the fast fluidization regime, the catalyst should be continuously introduced into the lower portion of the riser. In the fast fluidization regime, a catalyst volume fraction changes along the height within the riser, and there are a dense region in a lower portion of the riser and a dilute region in an upper portion of the riser.

Furthermore, when the velocity of a rising gas is further increased in the fast fluidization regime or the introduction of solid particles itself is decreased, since the catalyst volume in the riser is reduced, a transition to a lean-phase fluidization with pneumatic transport regime occurs. In the lean-phase fluidization with pneumatic transport regime, a catalyst volume fraction is very low and almost constant at all heights within the riser.

Here, the catalyst volume refers to a volume occupied by a catalyst in a given volume excluding voids, and when the catalyst is a porous catalyst, the catalyst volume includes the volume of macropores and micropores inside the catalyst.

Kunii and Levenspiel (1991, Fluidization Engineering) state that since the entrainment of a catalyst discharged from the riser occurs rapidly in the fast fluidization regime, the catalyst should be continuously injected in order to maintain normal operating conditions and, as shown in FIG. 2, defines characteristics of the fast fluidization regime as follows:

- At a short distance from an inlet at the bottom of the riser, the volume fraction of the catalyst is 0.2 to 0.4 with respect to the volume of the riser.
- From a lower portion of the riser to a specific height within the riser, the catalyst volume fraction is constant at about 0.2 at all heights within the riser. This region is referred to as a dense region.
- At an upper portion of the riser above the dense region, the volume of the catalyst gradually changes, and the volume fraction is in the range of 0.02 to 0.05.

The qualitative characteristics of the fast fluidization regime are the same throughout the change of the process, but the quantitative value of the catalyst volume changes. The quantitative value of the catalyst volume changes with physical properties of the catalyst such as density and a degree of sphericity, and also changes with physical properties of gas such as density and viscosity, which vary by gas type.

Therefore, a preferable fast fluidization regime that can be used for a circulating fluidized bed dehydrogenation process of a hydrocarbon compound according to the present invention is formed by maintaining a normal state in which a fixed amount of catalyst is continuously introduced into the riser while a gas flow rate in the riser is maintained to be higher than in a turbulent fluidization regime and lower than in a lean-phase fluidization with pneumatic transport regime, and in this case, a catalyst volume fraction changes along the height within the riser, and the fast fluidization regime may be described as a fluidization regime in which a dense region is present at a lower portion of the riser and a dilute region is present at an upper portion of the riser. The following describes how the fast fluidization regime is formed in more detail and defines the fast fluidization regime:

a) The gas velocity should be maintained to be no less than the gas flow rate required for allowing the catalyst to be entrained and smoothly discharged from the upper portion of the riser, and the catalyst should be continuously introduced into the lower portion of the riser.

b) As the gas flow rate increases under the above-described conditions, the catalyst volume fraction difference between a ¼ point and a ¾ point from the bottom of the riser is reduced, and it is required that the gas flow rate and a catalyst injection rate are controlled so that the catalyst volume fraction difference between the two points is maintained within the range of 0.02 to 0.04. The reactivity of the catalyst of the present invention is highly efficient, particularly in the fast fluidization regime, and when the volume fraction difference is less than 0.02, since the fluidization regime becomes closer to a lean-phase fluidization with pneumatic transport regime, yield may be lowered due to a high space velocity, and when the difference is more than 0.04, turbulence fluidization or bubbling fluidization may occur, which is undesirable.

In carrying out the process of producing an olefin-based hydrocarbon from a hydrocarbon mixture feedstock and preferably a hydrocarbon mixture including propane in an amount of 90% by weight or more using a circulating fluidized bed process according to the present invention, when gas velocity in the riser and a catalyst injection rate into the riser are adjusted to satisfy the above-described conditions so that the process is carried out in the fast fluidization regime, the maximum catalyst concentration can be provided in the riser. Therefore, based on this principle, it is possible to provide high conversion to and high selectivity for an olefin-based hydrocarbon and more preferably propylene.

Comparative Example: Lean-Phase Fluidization with Pneumatic Transport Regime

A. Construction of Cold Model

Figure 4:
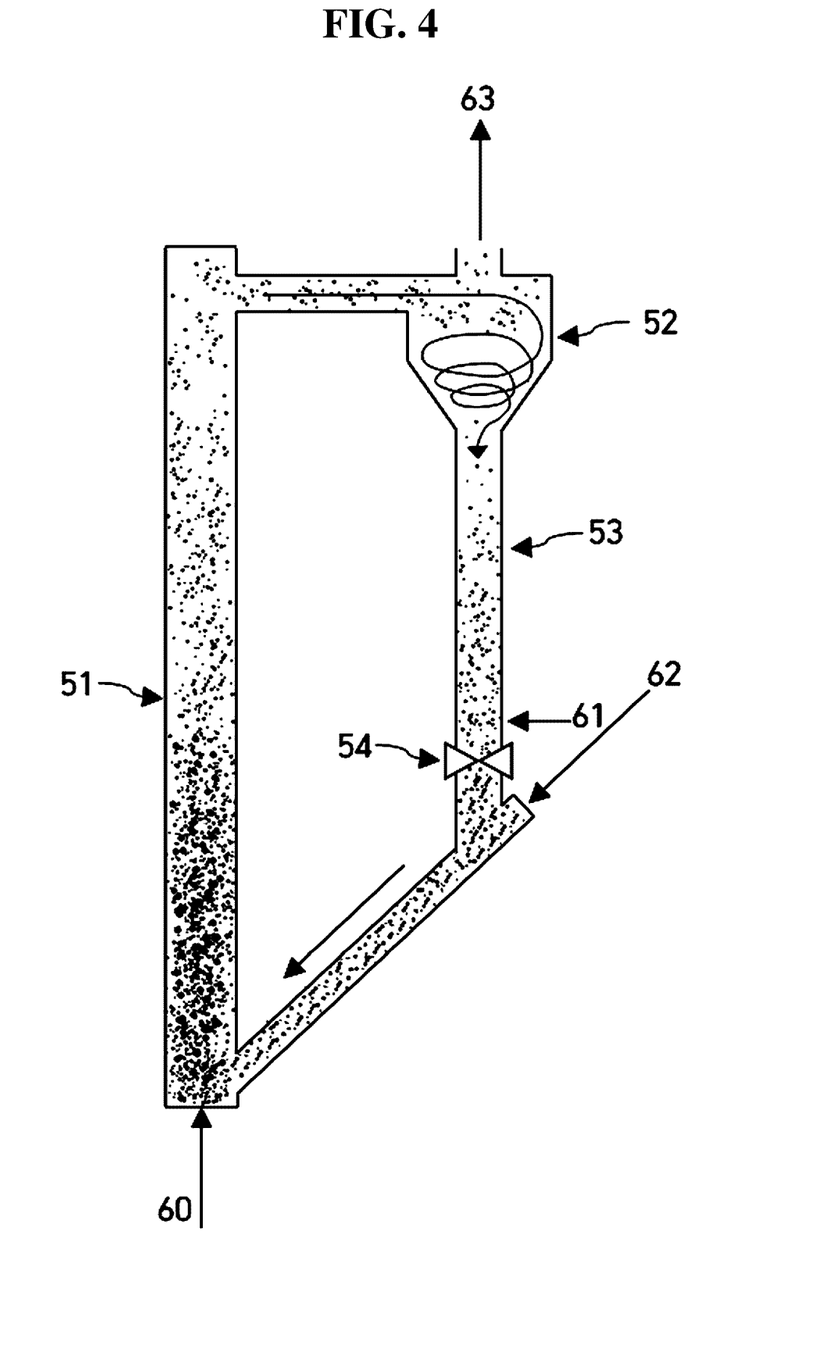
FIG. 4 is an image for schematically illustrating a fluidized bed cold model for experimenting with flow regimes at room temperature.

In order to identify types of flow regimes according to a change in gas velocity and catalyst injection rate at room temperature, a fluidized-bed cold model as shown in FIG. 4 was constructed. Solid particles that had passed through a slide valve 54 configured to control a solid circulation rate were introduced into a cold model riser 51 and then were moved upward along the riser by a main gas supplied through a line 60. After gas and solid were separated in a cold model cyclone, the gas was discharged as a flue gas through a line 63, and the solid was moved downward along a cold model stand pipe (line 53). In this case, the circulation of the solid was facilitated by the gas supplied through gas supply lines 61, 62. The cold model slide valve 54 controlled the amount of catalyst circulation through an opening ratio, that is, a degree to which a sleeve in the valve is opened.

In Comparative Example 1, a cold model riser having a height of 3.0 m and a diameter of 1.0 cm was constructed, and a stand pipe and a slide valve configured to facilitate catalyst circulation were constructed.

B. Catalyst

The catalyst used in the experiment was [15% Cr+0.25% $Na_2WO_4$)/Zr—$Al_2O_3$] and was produced as described below. The catalyst had a volume-average particle diameter of 78 microns and a particle size distribution consisting of 10% particles having a size of 60 microns or less, 80% particles having a size of 60 to 100 microns, and 10% particles having a size of 100 microns or more.

(1) Production of Support (Zr—$Al_2O_3$)

After adding 25 kg of water to 13.89 kg of Catapal B (alumina, commercially available from Sasol) and stirring for 30 minutes, 1.83 kg of $ZrO(NO_3)_2$ and 25 kg of water were added and stirred for an additional 2.5 hours. Subsequently, the resultant was spray-dried (supply rate: 0.56 g/min, atomizer: 6,000 rpm, inlet temperature: 208° C., outlet temperature: 125° C.), sieved (75 to 200 μm), and then calcined at 650° C. for six hours.

(2) Production of Catalyst [(1 to 15% Cr+0.1 to 1% $Na_2WO_4$)Zr—$Al_2O_3$]

Based on 10 g of the support (Zr—$Al_2O_3$) produced in Production Example 1, 0.19 to 3.39 g (1 to 15% by weight based on Cr) of $CrO_3$ (chromium trioxide, 99.9%) and 0.072 to 0.725 g (0.1 to 1% by weight based on Na) of $Na_2WO_4$ (sodium tungstate, dihydrate) were added to 5 g of water and stirred for one hour. A mixture of Cr and a $Na_2WO_4$ precursor was impregnated into 10 g of the support, dried at 120° C., and calcined at 850° C. for 10 hours, and thereby a catalyst of the present invention was obtained.

C. Fluidization Regime Experiment

Figure 5:
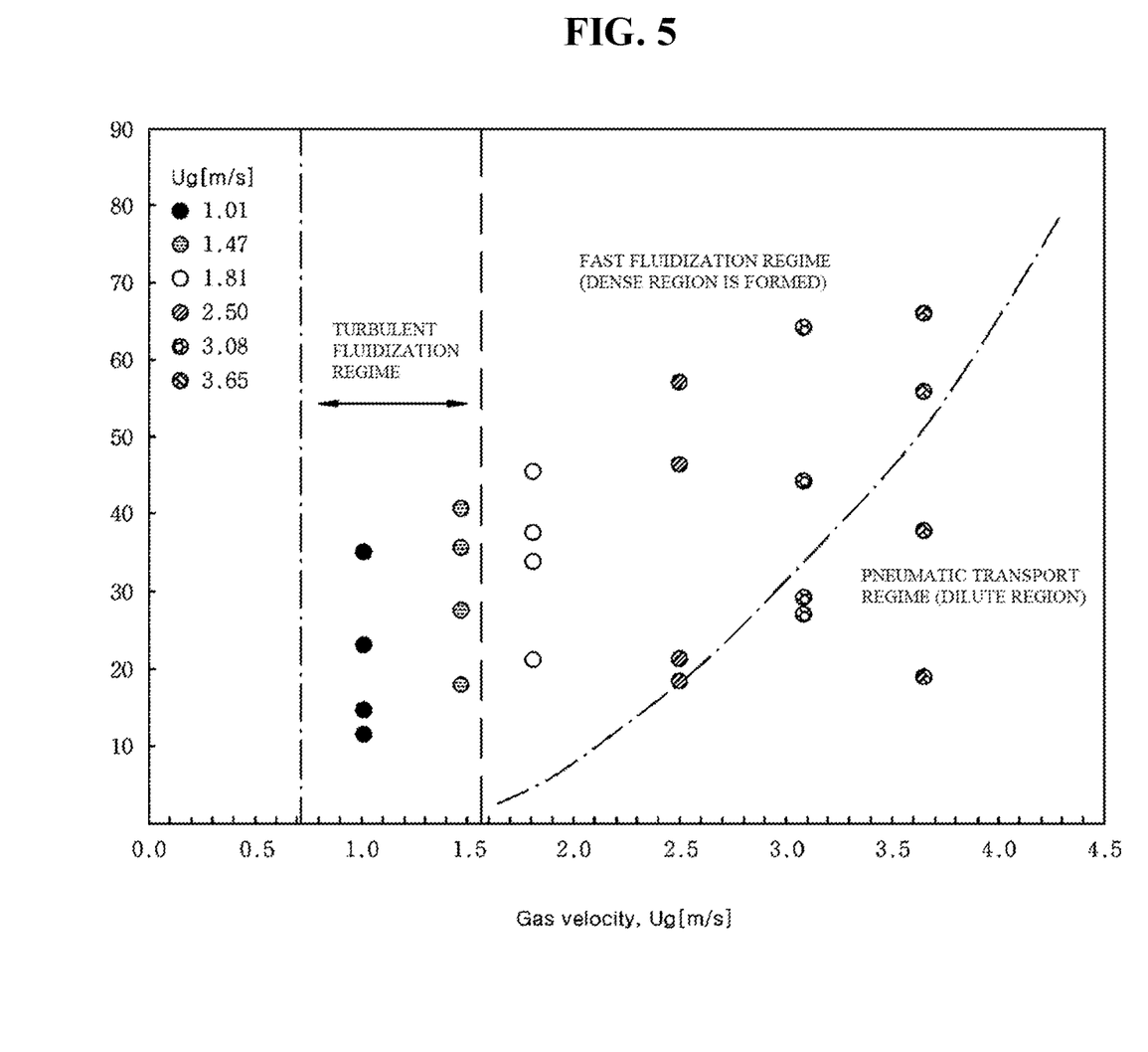
FIG. 5 is a graph illustrating the results of a cold model experiment according to Comparative Example 1, which shows a fast fluidization regime and a lean-phase fluidization with pneumatic transport regime according to changes in a flow rate and a catalyst circulation amount.

The experiment was performed at room temperature and normal pressure, and the catalyst was injected at a rate of 3.2 to 18.6 kg/hr through an inlet in the lower portion of the riser and allowed to circulate, and this rate corresponds to a rate of 11.5 to 65.8 kg/m²·s inside the riser. A gas was injected into a lower portion of the riser at a flow rate of 1.01 to 3.65 m/s, and then a particle concentration inside the reactor was monitored. Referring to the relationship between a flow rate and a catalyst circulation rate in FIG. 5, the fast fluidization regime which is appropriate for the present invention began where a gas velocity was 1.5 m/s or more, and in this case, it can be seen that the fast fluidization regime having a dense region in which a large number of catalyst particles are present in the reactor, favoring a catalytic reaction, can only be attained when at least a specific solid circulation rate is maintained.

Example 1: Fast Fluidization Regime

A. Construction of Cold Model

A cold model was constructed in the same manner as in Comparative Example 1, as shown in FIG. 4.

B. Catalyst

The same catalyst as used in Comparative Example 1 was used.

C. Fluidization Regime Experiment

Figure 6:
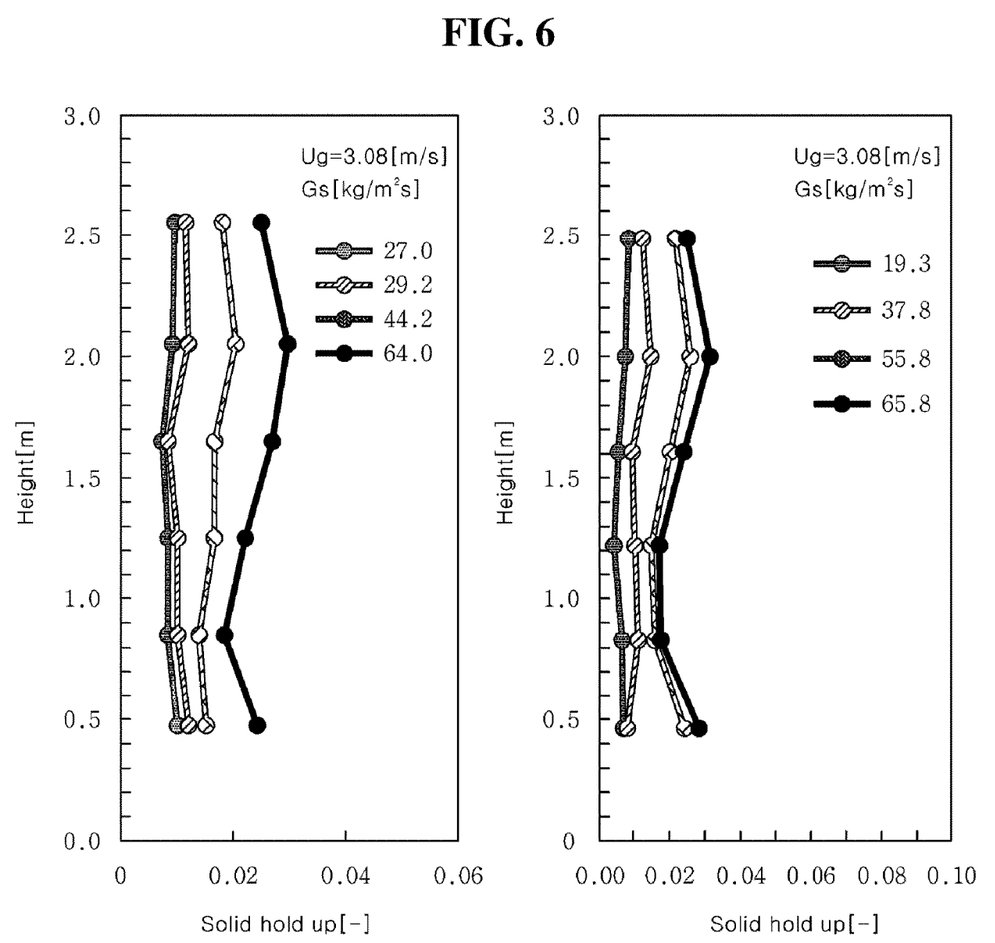
FIG. 6 is a graph illustrating the results of a cold model experiment according to Example 1, which shows catalyst volume fractions in a fast fluidization regime and a lean-phase fluidization with pneumatic transport regime.

The experiment was performed at room temperature and normal pressure, and the catalyst was injected at a rate of 5.4 to 18.6 kg/hr through an inlet in the lower portion of the riser and allowed to circulate, and this rate corresponds to a rate of 19.3 to 65.8 kg/m²·s inside the riser. A gas was injected into a lower portion of the riser at a flow rate of 3.08 to 3.65 m/s, and then the particle concentration distribution inside the reactor was monitored. Referring to a change in the particle concentration distribution according to changes in a flow rate and a catalyst circulation rate in FIG. 6, it can be seen that at all gas flow rates, as a solid circulation rate increases, a catalyst volume fraction changes near the boundary between a pneumatic transport regime and a fast fluidization regime shown in FIG. 5. Specifically, at gas flow rates of 3.08 m/s and 3.65 m/s, when a solid circulation rate is below the boundary between the fast fluidization regime and the pneumatic transport regime, the average catalyst volume fraction in the reactor is 1% or less, but when the solid circulation rate is increased to above the boundary between the fast fluidization regime and the pneumatic transport regime, a catalyst volume fraction at a portion below a ¼ point from the bottom of the riser sharply increases, and at the same time, an average catalyst volume fraction in the reactor increases to 2% or more. Therefore, it can be seen that a fluidization form that is a fast fluidization regime according to the definition of the present invention is exhibited.

Example 2

A. Catalyst

The same catalyst as used in Comparative Example 1 was used.

B. Production Process of Olefin

In Example 2, a circulating fluidized bed process was used to measure catalyst activity during the olefin production process as shown in FIG. 3. The circulating fluidized bed process was performed using a riser, a regenerator, a stripper, and a stabilizer. The riser had a height of 7 m and a diameter of 0.94 cm, the regenerator had a height of 1.5 m and a diameter of 12 cm, the stripper had a height of 2 m and a diameter of 10 cm, and the stabilizer had a height of 1.7 m and a diameter of 15 cm.

At an inlet of the riser, a hydrocarbon mixture feedstock including propane in an amount of 90% by weight or more, a dilution gas, and a catalyst were injected and mixed, and feedstock conditions were 700 g/hr and 590° C., and space velocity conditions were 8,200 ml/g·cat·hr and 630° C. In addition, the amount of catalyst injection was 88.1 kg/m²·s (same as the cold model of Comparative Example 1) when considering the cross-sectional area of the riser.

The velocity of the total gas vaporized at the inlet of the riser in Example 2 was the same as in Example 1, and when considering the density and velocity of the gas, it was determined that the fluidization characteristics in the risers of Example 1 and Example 2 were the same, and therefore, it can be seen that the fluidization regime of Example 2 was a fast fluidization regime.

In addition, in Example 2, the residence time of the gas in the riser was about two seconds as determined based on a gas velocity at an outlet of the riser, and a ratio of the weight of regenerated catalyst introduced per hour to the weight of feedstock introduced into the inlet of the riser per hour was 53.

As the feedstock passed through the riser, a dehydrogenation reaction occurred in the fluidized bed, and outlet conditions of the riser were 599° C. and 2 barg. Subsequently, after the mixture which had passed through the riser was separated into the catalyst and a remainder in the stripper at 500° C., the catalyst was circulated to the regenerator, and the remainder was introduced into the stabilizer. The catalyst which had been injected into the regenerator came into contact with air and thus was regenerated at 650° C., and the regenerated catalyst was reintroduced into the riser. Meanwhile, the remainder which had been introduced into the stabilizer was separated into gas components and liquid components at −10° C.

The results of the experiment are summarized below in Table 1.

TABLE 1

| | |
|---|---|
| Space velocity (weight hour space velocity (WHSC); ml/g · cat · hr) | 8,200 |
| Reaction temperature (° C.) | 640 |
| Conversion (wt %) | 37.4 |
| Selectivity (wt %) | 80.2 |
| Propylene yield (wt %) | 30 |
| CO yield (wt %) | 0.9 |
| $CO_2$ yield (wt %) | 0.5 |

Comparative Example 2

A. Production of Catalyst

A catalyst was produced in the same manner as in Example 2.

B. Production Process of Olefin

In Comparative Example 2, the same circulating fluidized bed process as in Example 2 was performed except for using a different riser. The riser used in Comparative Example 2 had a height of 7.0 m and a diameter of 0.94 cm.

The same feedstock as in Example 2 was used, and feedstock conditions were 700 g/hr and 580° C., and space velocity conditions were 21,000 ml/g·cat·hr and 640° C.

In the case of Comparative Example 2, it was determined that the fluidization characteristics in the risers of Comparative Example 1 and Comparative Example 2 were the same as determined based on the density and viscosity of the gas, and therefore, it can be seen that the fluidization regime of Comparative Example 2 was a lean-phase fluidization with pneumatic transport regime.

Meanwhile, in Comparative Example 2, a gas residence time, a ratio at which the feedstock introduced into the inlet of the riser was diluted, and a ratio of the weight of regenerated catalyst introduced per hour to the weight of feedstock introduced into the inlet of the riser per hour were the same as in Comparative Example 1.

The results of the experiment are summarized below in Table 2.

TABLE 2

| | |
|---|---|
| Space velocity (WHSC; ml/g · cat · hr) | 21,000 |
| Reaction temperature (° C.) | 630 |
| Conversion (wt %) | 29.9 |
| Selectivity (wt %) | 78.9 |
| Propylene yield (wt %) | 23.6 |
| CO yield (wt %) | 0.8 |
| $CO_2$ yield (wt %) | 0.7 |

When the reaction product yields of Comparative Example 2 and Example 2 are compared, it can be seen that, in Example 2, a conversion to an olefin and the selectivity for the olefin were high, and a conversion to propylene was particularly high. These results confirm that the contact capable of causing a reaction is controlled by controlling a residence time in a fast fluidization regime which is significant in the present invention. In addition, in the present invention, since propylene yield is greatly improved, incremental profits from raw materials are increased, and thus economic efficiency is greatly improved.

That is, in the cold models of Comparative Example 1 and Example 1, gas velocity and a catalyst injection amount were controlled, and this is the same setting as the reaction conditions of catalyst fluidization regimes of Comparative Example 2 and Example 2. It is common to identify a fluidization regime in a fluidized bed reactor using such a cold model, and it can be understood that in Comparative Example 2, a lean-phase fluidization with pneumatic transport regime was exhibited in the riser as in Comparative Example 1, and in Example 2, a fast fluidization regime was exhibited in the riser as in Example 1.

Although exemplary embodiments of the present invention have been described in detail above, it will be obvious to those of ordinary skill in the art that the scope of the present invention is not limited to the embodiments and that various modifications and changes can be made without departing from the technical spirit of the present invention described in the claims.

The present invention is capable of providing an olefin production process using a fluidized bed, which has higher economic efficiency and higher productivity than the conventional process.

The invention claimed is:

1. A method of producing an olefin using a circulating fluidized bed process, comprising:
    (a) supplying a hydrocarbon mixture including propane and a dehydrogenation catalyst to a riser which is in a state of a fast fluidization regime, and thus inducing a dehydrogenation reaction;
    (b) separating an effluent from the dehydrogenation reaction into the catalyst and a propylene mixture;
    (c) stripping, in which a residual hydrocarbon compound is removed from the catalyst separated in step (b);
    (d) mixing the catalyst stripped in step (c) with a gas containing oxygen and thus continuously regenerating the catalyst;
    (e) circulating the catalyst regenerated in step (d) to step (a) and thus resupplying the catalyst to the riser by adding the catalyst regenerated in step (d) at the bottom of the riser; and
    (f) cooling, compressing, and separating the propylene mixture, which is a reaction product separated in step (b), and thus producing a propylene product,
    wherein the dehydrogenation catalyst includes: a support including alumina and an auxiliary support component; and a main catalyst including an active metal supported on the support, and includes a promoter including an alkali metal and a Group 6B transition metal.

2. The method of claim 1, wherein the fast fluidization regime is a fluidization regime in which a dense region is present at a lower portion of the riser and a dilute region is present at an upper portion of the riser, and is a steady state in which a fixed amount of catalyst is continuously introduced into the riser while a gas flow rate in the riser is maintained to be higher than in a turbulent fluidization regime and lower than in a lean-phase fluidization with pneumatic transport regime.

3. The method of claim 2, wherein, in the fast fluidization regime, a) a gas velocity that is no less than a gas flow rate required for the catalyst continuously introduced through a lower portion of the riser to be entrained and smoothly discharged through an upper portion of the riser is maintained, and b) the gas velocity and a catalyst injection rate are adjusted so that a catalyst volume fraction difference between two points is maintained within a range of 0.02 to 0.04.

4. The method of claim 3, wherein the catalyst volume fraction difference between a ¼ point and a ¾ point from a bottom of the riser is maintained within a range of 0.02 to 0.04.

5. The method of claim 1, wherein the hydrocarbon mixture includes propane in an amount of 90% by weight or more.

6. The method of claim 1, wherein an average size of the catalyst is in a range of 20 to 200 microns.

7. The method of claim 6, wherein the average size of the catalyst is in a range of 60 to 120 microns.

8. The method of claim 1, wherein a temperature of a lower portion of the riser is in a range of 500 to 650° C., a temperature of an upper portion of the riser is in a range of 450 to 600° C., and the temperature of the lower portion of the riser is maintained to be higher than the temperature of the upper portion of the riser.

9. The method of claim 1, wherein a pressure in the riser is in a range of −1 to 5 kg/cm$^2$·g.

10. The method of claim 1, wherein a residence time of the hydrocarbon mixture in the riser is in a range of 0.1 to 500 seconds for the dehydrogenation reaction to occur in the riser.

11. The method of claim 10, wherein the residence time is in a range of 0.1 to 50 seconds.

12. The method of claim 11, wherein the residence time is in a range of 0.5 to 5 seconds.

13. The method of claim 1, wherein a weight ratio obtained by dividing a weight of the catalyst resupplied to a lower portion of the riser in step (e) by a weight of the hydrocarbon mixture is in a range of 10 to 100.

14. The method of claim 13, wherein the weight ratio is in a range of 20 to 60.

15. The method of claim 1, wherein the auxiliary support component includes one or more selected from among zirconium and phosphorus (P).

16. The method of claim 1, wherein the auxiliary support component is zirconium, and a molar ratio of the zirconium to aluminum (i.e., Zr:Al) in the alumina is in a range of 0.01 to 0.1.

17. The method of claim 1, wherein a component of the active metal includes one or more selected from chromium, vanadium, manganese, iron, cobalt, molybdenum, copper, zinc, cerium, and nickel.

18. The method of claim 1, wherein a component of the active metal is chromium, and the chromium accounts for 1 to 20% of a weight of the catalyst.

19. The method of claim 1, wherein the alkali metal is sodium.

20. The method of claim 1, wherein the Group 6B transition metal is tungsten.

21. The method of claim 1, wherein the promoter is included in an amount of 0.01% by weight or more and less than 1% by weight.

22. The method of claim 1, the alumina support has a γ or θ phase and a surface area of 80 to 300 m$^2$/g in a producing temperature range of 550 to 850° C., which is greater than or equal to the dehydrogenation reaction temperature.

23. The method of claim 1, wherein the dehydrogenation catalyst is produced by a method including:
providing a support including an auxiliary support component and alumina;
allowing a main catalyst including an active metal to be supported; and
drying and calcining the support on which the main catalyst is supported,
wherein a promoter is additionally supported, and the dehydrogenation catalyst is produced by mixing (a) the promoter including an alkali metal and a Group 6B transition metal, and (b) the main catalyst with the support at the same time, or by impregnating the promoter into the support immediately after the drying and then performing drying and calcining, or by impregnating the promoter into the support immediately after the calcining and then performing drying and calcining.

24. The method of claim 23, wherein the drying is performed at a temperature of 100 to 150° C.

25. The method of claim 23, wherein the calcining is performed at a temperature of 700 to 850° C.

26. The method of claim 1, wherein
the auxiliary support component includes one or more selected from among zirconium and phosphorus (P);
a component of the active metal includes one or more selected from chromium, vanadium, manganese, iron, cobalt, molybdenum, copper, zinc, cerium, and nickel;
the alkali metal is sodium; and
the Group 6B transition metal is tungsten.

* * * * *